United States Patent [19]

Burgdorfer

[11] Patent Number: 5,421,214
[45] Date of Patent: Jun. 6, 1995

[54] AIR SAMPLER FOR CLEAN ROOMS

[75] Inventor: Roger D. Burgdorfer, Olathe, Kans.

[73] Assignee: Central Biomedia, Inc., Lenexa, Kans.

[21] Appl. No.: 8,698

[22] Filed: Jan. 25, 1993

[51] Int. Cl.$^6$ ............................................. G01N 15/00
[52] U.S. Cl. ............................... 73/863.22; 73/28.05; 435/294
[58] Field of Search ........... 73/863.21, 863.22, 863.23, 73/863.24, 863.25, 864.71, 864.34, 28.05; 435/294, 301; 55/270

[56] References Cited

U.S. PATENT DOCUMENTS

| | | | |
|---|---|---|---|
| 3,127,329 | 3/1964 | Andersen | 435/294 |
| 3,684,660 | 8/1972 | Kereluk et al. | 435/294 |
| 3,968,012 | 7/1976 | Jones | 435/294 |
| 3,980,524 | 9/1976 | Reuter | 435/294 |
| 4,663,293 | 5/1987 | Hempel et al. | 435/294 |

FOREIGN PATENT DOCUMENTS 1643988  4/1991  U.S.S.R. ........................... 73/863.21

Primary Examiner—Hezron E. Williams
Assistant Examiner—Nashmiya Ashraf
Attorney, Agent, or Firm—Kokjer, Kircher, Bowman & Johnson

[57] ABSTRACT

A device for measuring airborne contaminants. The device includes a housing which includes an air passage chamber having an inlet and an outlet. An air movement mechanism, typically an impeller blade powered by a motor, is located within the air movement chamber to cause movement of air from the inlet to the outlet. A support is provided adjacent the outlet such that air passing through the air passage chamber will impinge upon the support. The support is formed such that it may hold standard, commercially available, collection elements. Control devices are provided to operate the air movement mechanism, and may include a timer which automatically ceases operation of the air movement mechanism after a predetermined time has expired, with this predetermined time being calculated to correspond to a predetermined or desired volume of air passed out of the air passage chamber. This arrangement eliminates the need to purchase specially designed collection elements, thus reducing the cost of determining if airborne contaminates are present.

10 Claims, 1 Drawing Sheet

AIR SAMPLER FOR CLEAN ROOMS

BACKGROUND OF THE INVENTION

1. Field of the Invention

The present invention relates in general to an apparatus for the measurement of the amount of airborne contamination. In particular, the present invention relates to an improved device for use in a medical clean room which will impact air upon a microbial growth medium, such that the growth medium may be cultured to determine the presence of airborne microbial particles within such clean room.

2. Description of the Related Art

It is a common practice to assemble, test and package various devices or articles within "clean rooms" to avoid or at least substantially reduce contamination of the articles with dust and/or biological contaminants, such as viable microbes. One particular application of such a clean room is the assembly of sterile medical devices or products. Currently, federal regulations allow a minimum acceptable number of viable airborne microbial particles per cubic foot of air within such a clean room.

Several devices are commercially available which will allow the determination of the amount of such airborne microbes within clean rooms. These devices generally consist of a housing which supports a motor to drive a shaft, from which extends a plurality of vanes. The housing includes an inlet port to allow air to enter and a peripheral wall surrounding the radially outer ends of the vanes such that air is drawn through the inlet and moved radially outward by the vanes to impact upon the peripheral wall. In use, an strip coated with agar growth medium is mounted on the interior of the peripheral wall such that the air displaced by the vanes will impact upon the agar strips and any airborne microbial material will be trapped thereon.

This operation is performed in the clean room and the agar strip thereafter removed from the device and cultured. This culture will reveal the amount of viable microbes within the volume of air impacted upon the agar strip, such that when the vanes are operated to displace a known amount of air the number of microbes per cubic foot may be calculated and thus determine if the clean room meets federal standards.

While this arrangement is serviceable, it is difficult to place and remove the agar strips about the interior of the peripheral wall due to the proximity of the vanes. Additionally, the agar strips are specially designed to be used within the specific device produced by that manufacturer, and must be purchased from the manufacturer of the device. Such strips are typically relatively expensive, thus increasing the cost of operating a clean room.

SUMMARY OF THE INVENTION

An object of the present invention is to provide a device which may accurately determine the amount of airborne contaminants within a given volume of air.

Another object of the present invention is to provide a device which may determine the amount of microbial contamination within a given volume of air.

A further object of the present invention is to provide such a device which employs an object upon which the contaminants are deposited, and which allows simple and easy placement and removal of the object upon which the contaminants are deposited.

Another object of the present invention is to provide such a device which employs standard, commercially available culture plates as the object.

Yet another object of the present invention is to provide a device for measuring airborne contamination within a given volume of air which directs the air through a conduit to impinge upon a collection surface of the object.

These and other objects are achieved by a device for measuring airborne contaminants. The device includes a housing which includes an air passage chamber having an inlet and an outlet. An air movement mechanism, typically an impeller blade powered by a motor, is located within the air movement chamber to cause movement of air from the inlet to the outlet. A support is provided adjacent the outlet such that air passing through the air passage chamber will impinge upon the support. The support is formed such that it may hold standard, commercially available, collection elements. Control means are provided to operate the air movement mechanism, and may include a timer which automatically ceases operation of the air movement mechanism after a predetermined time has expired, with this predetermined time being calculated to correspond to a predetermined or desired volume of air passed out of the air passage chamber. This arrangement eliminates the need to purchase specially designed collection elements, thus reducing the cost of determining if airborne contaminates are present.

BRIEF DESCRIPTION OF THE DRAWINGS

The objects and features of the invention noted above are explained in more detail with reference to the drawings, in which like reference numerals denote like elements, and in which.

DETAILED DESCRIPTION OF THE INVENTION

Figure 1:
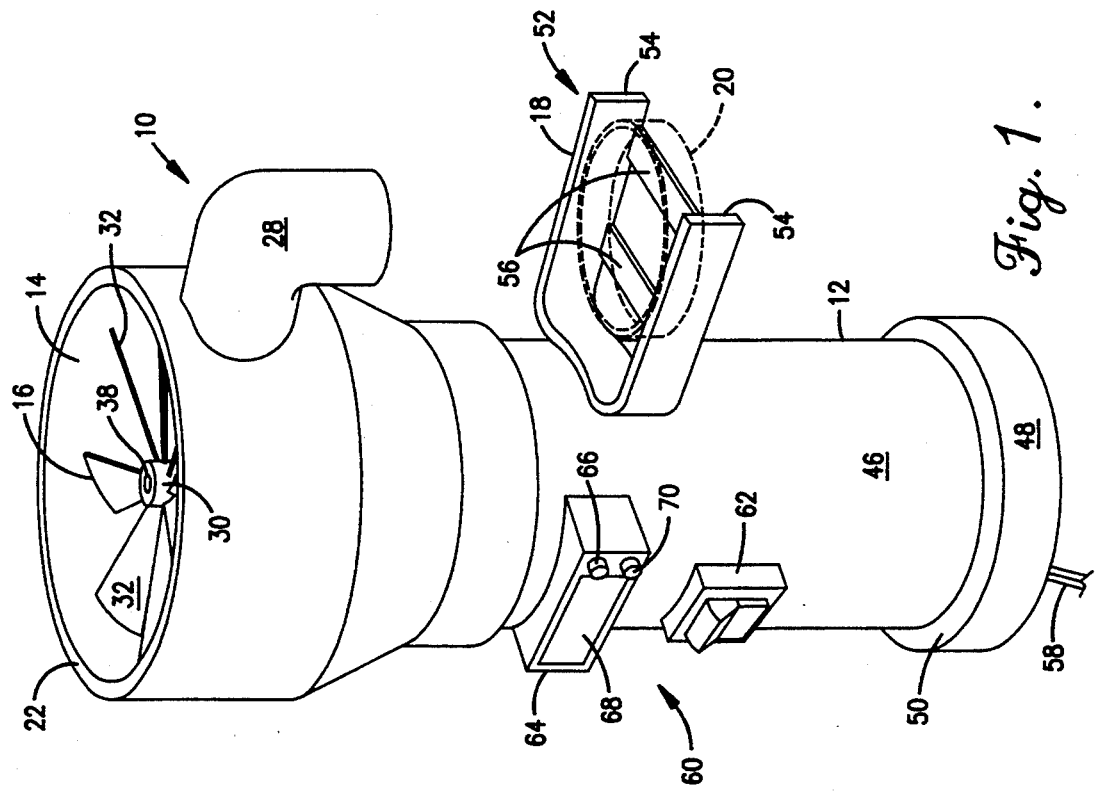
FIG. 1 is a perspective view of device according to the present invention.

With reference to FIG. 1, a device according to the present invention is generally designated by reference numeral 10. The device 10 generally consists of a housing 12 having an air passage chamber 14. A means or mechanism for causing air movement 16 is located within the air passage chamber 14, and there is also provided a support 18 located such that the air moved by the means or mechanism 16 impinges upon the support so that an object 20 received upon the support will also be impinged upon by the air flow.

The housing 12 may be formed of many materials, such as aluminum or stainless steel, but it is preferred that the housing be formed of plastic for light weight and reduced cost. As noted above, the housing 12 includes the air passage chamber 14. The air passage chamber may have any size or configuration so long as it is compatible with the means or mechanism for moving air, and so long as it has an inlet 22 and an outlet 24 through which the air may pass as it is moved by the means or mechanism 16. As is shown in the Figures, the air passage chamber 14 may include an upstanding peripheral wall 26, with such peripheral wall having a tubular configuration (although other cross-sections are possible). The upper free end of the peripheral wall 26 defines the inlet 22 for the chamber 14. Extending radially outward from the wall 26 is an air conduit 28 in communication with the chamber 14, with the free end of the air conduit defining the outlet 24. As is shown in the drawings, the air conduit 28 may include a downward bend such that it is directed downward at the outlet 24, and the air exiting from the outlet will have a downward velocity.

The means or mechanism 16 for moving air is located within the air passage chamber 14. While this means or mechanism could take many forms, it is preferred that it take the form of a rotating impeller or fan having a centrally located hub 30 and a plurality of radially extending vanes or blades 32 which will cause a flow of air as the vanes and hub rotate together, with this flow of air being directed from the inlet 22 through the chamber 14 and exiting from the outlet 24.

The axis of rotation of the hub 30 is substantially coincident with the longitudinal axis of the tube defined by the peripheral wall 26, such that the free ends of the vanes 32 have a relatively close tolerance with the interior face of wall 26. In the embodiment shown, the vanes are canted such that the leading edge is vertically higher than the trailing edge, with the vanes being located at the upper edge of the air conduit 28. By this arrangement rotation of the hub will cause the vanes to produce a downward flow of air which will enter and pass through the conduit 28. Other arrangements are, however, possible. For example, the vanes could be vertically oriented and be centrally located of conduit 28, such that the vanes have a mainly radial output of air which is directed into the conduit.

Figure 2:
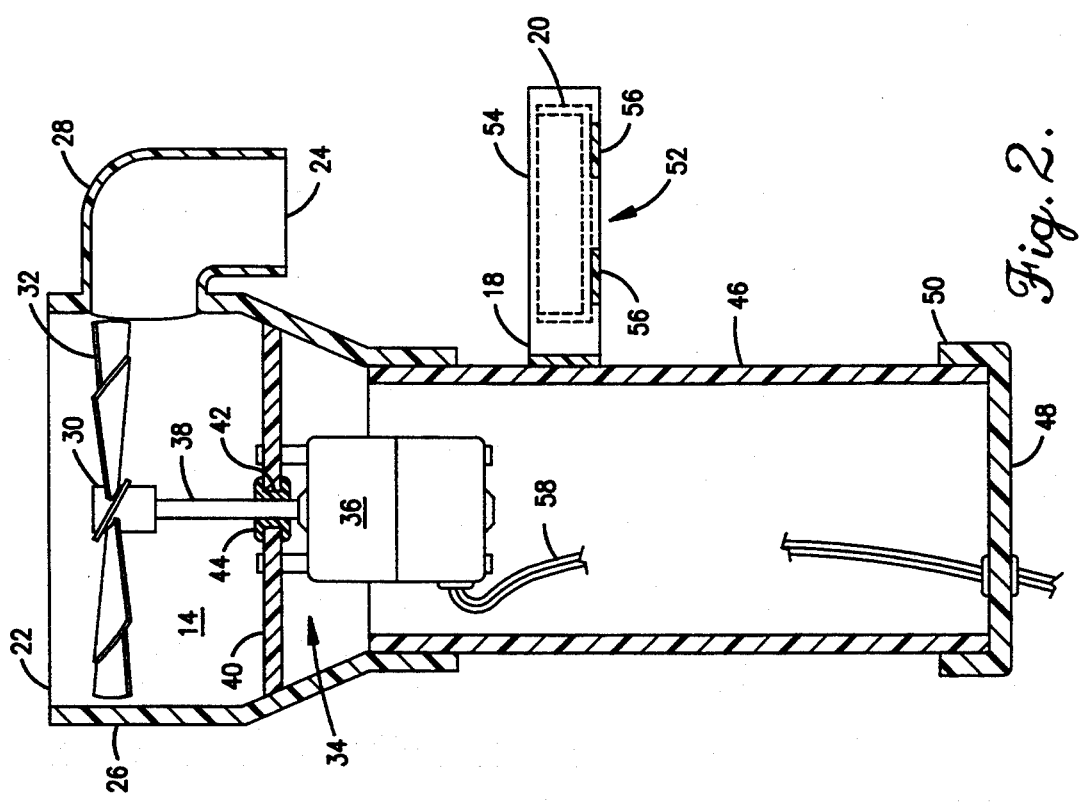
FIG. 2 is a cross-sectional side view of the device of FIG. 1.

Another variation could be to provide a second hub 30 with associated second vanes 32 located below the hub shown in FIG. 2, and with the vanes having an opposite orientation. The peripheral wall could be provided with peripherally spaced openings to define further air inlets 22 near the lower end of the air passage chamber 14, with the second vanes 32 being located adjacent the lower edge of the conduit 28. With this arrangement, both sets of vanes would tend to force air into the conduit 28, reducing the time necessary to test a given volume of air. As may be seen, virtually any arrangement for moving air may be employed, although those which are easy to maintain in a sterile condition are greatly preferred. For example, the single hub and vane arrangement shown in FIGS. 1 and 2 would be much easier to clean and provide fewer hidden surfaces to sterilize compared to an arrangement having two hubs and sets of vanes.

The means or mechanism 16 for moving air additionally includes an associated drive mechanism 34. In the embodiment shown, the drive mechanism consists of an electric motor 36 having a driven shaft 38 extending therefrom. The shaft 38 fixedly mounts the hub 30 such that operation of motor 36 will cause the desired rotation of the hub 30 and vanes 32.

The motor 36 is mounted to the housing 12, however, to reduce contamination of air passing through the chamber 14 from dust or other contaminants produced by the motor 36, it is preferred that the drive mechanism 34 be as isolated from the air passage chamber 14 as is possible. In the embodiment shown, this is effected by use of a barrier plate 40 (FIG. 2) sealed to the housing 12 at a position spaced from the inlet 22 to thus define a portion of the air passage chamber 14. In particular, the hub and vanes 30 and 32 are located intermediate of the inlet 22 and the barrier plate 40 such that the drive mechanism 34, located on the opposite side of barrier plate 40, is as removed as possible from the air passage chamber 14.

As the motor 36 employs a shaft 38 for connection to the hub 30, the shaft 38 extends through a shaft opening 42 to allow it to extend into the chamber 14. To reduce contamination through this shaft opening 42, it is preferred that the opening 42 have a peripheral size which is greater than that of the shaft 38 and that a seal 44 be interposed between the exterior of shaft 38 and interior of shaft opening 42 with a close sliding fit. As may be envisioned, this will greatly reduce the amount of contamination which may pass through the barrier plate 40 and into the air passage chamber 14.

Other drive arrangements are of course possible, some of which provide a reduced possibility of contamination. For example, the barrier plate 40 could have no shaft hole, yet include a rigid circular rod extending therefrom into the air passage chamber 14 at the position shown in FIG. 2 for shaft 38. This rod would rotatably mount the hub 30, with a cap being located on the free end of the rod to prevent the hub from being removed therefrom. Appropriate low friction material could be provided on the exterior of the rod or the interior of the hub, and possibly between the lower end of the hub and barrier plate 40, to ease rotation. The hub 40 could then be provided with one or more permanent magnets imbedded in its lower end adjacent the barrier plate 40. An electric motor could be located at a position similar to that shown in FIG. 2, with the drive shaft of such motor mounting a pair of radially spaced permanent magnets at a position such that the barrier plate 40 is interposed between the shaft of the drive motor and the hub 30. When the motor 36 is operated, the magnetic fields of the permanent magnets rotated by the motor would tend to cause the permanent magnets imbedded within the hub 30 to rotate therewith, causing rotation of the hub 30 and vanes 32, in a manner similar to other magnetic induction motors. Other means for producing the desired magnetic fields to cause movement of the permanent magnets imbedded within the hub 30 could, of course, be employed. This magnetic induction arrangement has the advantage that the air passage chamber 14 is totally isolated from the motor 36 or other magnetic field producing means, dramatically reducing the possibility of contamination of the air passage chamber and thus the air moving through the chamber. This can also aid in sterilization, as discussed below.

To further reduce the possibility of contamination by the drive mechanism, the housing 12 is extended such that it will fully encase the motor 36 in a substantially air- and/or water-tight manner. In the embodiment shown, this is achieved by extending the peripheral wall 26 downward below the barrier plate 40, possibly with an inward transition, and sealingly connecting the lower end of the peripheral wall 26 to a support tube 46. The lower end of the support tube 46 is sealed with a bottom plate 48 which may include an upstanding peripheral lip 50 which surrounds and is sealed to the exterior of support tube 46. While these various portions of the housing 12 which encase the motor 36 have been shown as tubular or circular, other arrangements are of course possible, such as elliptical or square. It is preferred, however, that the outer periphery of the support tube 46 be of a size and shape, and the support tube have a length, such that it may be manually grasped by a user to hold the device 10. This will be discussed more fully below.

With this arrangement the contaminants produced by the drive mechanism will be sealed within the housing and will not influence the samples gathered with the device. Additionally, this will aid in allowing the device to be immersed for cleaning or sterilization. This is especially true where magnetic induction is employed, as the possibility of contamination egress or cleanser ingress through the seal 44 is eliminated.

Mounted upon the exterior of the housing 12 at a position adjacent the outlet 24 of the air passage chamber is a sample support 52. The sample support 52 is of a size and configuration to readily and at least somewhat securely support the object 20 used to collect the sample.

In its preferred use, the device 10 will be employed with an object 20 in the form of a standard agar plate of the commonly type employed throughout laboratories and readily available from numerous commercial suppliers. Currently, such an agar plate consists of a standard circular petri dish having an upstanding peripheral lip with a layer of agar growth medium or equivalent coated upon at least a portion of its interior surface, as is very well known. As such, the sample support 52 preferably has a size and configuration to receive such an object 20.

To this end, the sample supports 52 consists of a pair of cantilevered side walls 54 reinforced by a pair of spaced support bars 56 extending between the side walls 54. The support bars 56 will serve to support the object 20 from below, while the side walls 54, which extend vertically upward with respect to the support bars 56, provide lateral support for the object 20. The connection of the sample support 52 to the housing 12 will result in the housing 12 (or a mounting bar extending between the side walls 54) forming a further barrier against movement of the object 20 radially inward of the housing 12. The radially outer free ends of the side walls 54 may include an upstanding end wall (not shown) extending therebetween to define an upwardly opening cavity in the sample support to securely retain the object 20 therein. However, it is preferred that no such end wall be employed such that the sample 20 may be slid radially inward of the sample support into the operative position shown in the figures.

As noted above, the sample support 52 is located opposite the outlet 24, such that the object 20, when in the operative position upon the sample support, will also be opposite the outlet 24 and the air exiting from the air passage chamber will thus impinge upon the object 20. The spacing between the outlet 24 and the sample support 52 will vary depending upon the size and orientation of the outlet 24 and upon the size of the object 20. To maintain ease of calibration, it is preferred that the air exiting the outlet 24, which will be somewhat turbulent and tend towards an expanding frusto-conical configuration as it leaves the outlet, fully impinge within the boundaries of the object 20, and more specifically upon the particular portion of the object 20 which includes the agar growth medium. The particular placement of the sample support for a given outlet orientation and object 20 may be readily determined using a wind tunnel smoke generator placed adjacent the outlet 24.

For operation, the drive mechanism 34 is of course operatively connected to a power source, such as compressed air, pressurized hydraulic fluid, or an electrical power source. In the present embodiment, the drive motor 36 is connected to an electrical power outlet via wiring 58, although the wiring 58 could be connected to a battery source located within the housing 12. While this is all that is strictly necessary, and operation of the motor 36 could be effected by connecting or disconnecting the wires 58 with the power outlet, it is preferred that the device 10 include control means 60 for controlling the operation of the drive mechanism 34. As shown in FIG. 1, the control means 60 may include a manual on/off switch 62 mounted upon the exterior of the housing and operatively connected to the motor. More preferably, the switch 62 is mounted upon the support tube 46 at a position readily accessible by a thumb of the user when the support tube is manually grasped by the user.

Alternatively or additionally, the control means 60 may include a timer mechanism 64. The timer 64 will include an appropriate start/stop button 66 and a display area 68 which will visually display the output of the timer and which may be LCD, LED, or other display arrangements.

In its most simple arrangement, the timer 64 will not be operatively connected to the on/off switch 62 such that the user must enable the timer by actuation of button 66 at the same moment that the switch 62 is operated, with the operator viewing the display area 68 to determine the proper time to again operate the switch 62 to deactivate the device 10. In this most simple form, the timer 64 could of course be deleted, with the operator simply viewing a wall clock or stop watch or other chronometer.

In more sophisticated embodiments, the timer 64 may be operatively coupled with the on/off switch 62 for automatic control of the drive mechanism 34. For example, the timer and switch 62 may be connected such that operation of the switch 62 will place the device in a standby mode, with operative power being supplied to the drive mechanism 34 only upon the operator pressing the start/stop button 66 of the timer 64. The timer 64 could then automatically count down the desired time period and automatically deactivate the drive mechanism upon expiration of this time period. In such an arrangement, it is preferred that the timer 64 include a set button 70 which, possibly in connection with other buttons (not shown), will allow the user to determine and set the desired time period for operation of the drive mechanism. Other arrangements are of course possible and encompassed by the present invention.

During operation, the operator will place an appropriate object 20 upon the sample support 52 and manually grasp the device 10 by the housing 12 to manually move it to the desired position for taking an air sample. Alternatively, the device 10 may be mounted upon a stand or support, or may merely rest upon a flat surface during the taking of the sample. The operator will then activate the drive mechanism 34 by use of the on/off switch 62 and/or the timer 64. When the predetermined time period has elapsed, the drive mechanism will be deactivated manually or automatically and the object 20 removed from the sample support 52.

During the taking of the sample, air from the surrounding area is drawn in through the inlet 22 and expelled out of the outlet 24 by the means or mechanism 16 for moving air, with this air being impacted upon the object 20 such that any contaminants within the expelled air are trapped upon the collection surface of the object 20, typically the agar growth material. When completed, the object 20 may be appropriately identified, such as by writing a control number upon the object, and then studied at a remote location to determine the presence of contaminants. This may include microscopic evaluation of the object 20, and in particular, the agar growth material, possibly after a waiting period to allow culturing of any microbial contamination.

The predetermined time period is typically set such that a desired volume of air will impact upon the object 20 and in particular the growth material therein, such that the amount of contamination per given volume of air may be determined to meet federal or other standards. To determine this time period, the device 10 may be operated while an anemometer is employed to determine the velocity of air expelled from the outlet 24. Multiplying this velocity by the cross-sectional area of the outlet 24 will yield a volumetric air flow which may be used as a divisor with the desired air volume to yield a necessary operation time to pass the desired volume of air from the outlet 24.

While specific embodiments have been shown and discussed, various modifications may of course be made. In particular, the shape of the housing may be altered considerably, such as to include handles, support legs, protective grating over the inlet 22 or other elements.

From the foregoing it will be seen that this invention is one well adapted to attain all ends and objects hereinabove set forth together with the other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawing is to be interpreted as illustrative, and not in a limiting sense.

What is claimed is:

1. A device for taking air samples to determine airborne contamination by depositing airborne contaminate upon an object, comprising:

housing having an interior and an exterior, and including an air passage chamber having an air inlet and an air outlet;

means for moving air, said means being mounted to said housing and having at least a portion thereof located within said air passage chamber intermediate said inlet and said outlet to thereby cause air to be drawn into said interior through said inlet and expelled from said chamber and housing through said outlet; and a sample support adapted to receive and support the object, said support being mounted on said exterior of said housing adjacent said outlet, downstream from said outlet in a direction of the air expelled therefrom, in a position such that at least a portion of the air expelled from said outlet impinges upon said object subsequent to the air being expelled from said outlet.

2. A device as in claim 1, in combination with the object, said object consisting of a circular petri dish having an upstanding peripheral wall and a microbial growth medium deposited therein.

3. A device as in claim 1, wherein said housing includes a peripheral wall surrounding, and at least partially defining, said air passage chamber, and wherein said means for moving air includes a hub having a plurality of radially extending vanes, said hub being rotatably connected to said housing, and further includes a drive mechanism operatively connected to said hub to selectively cause rotation of said hub, and thus said vanes, with respect to said housing.

4. A device as in claim 3, wherein said housing further includes a conduit extending from, and opening into, said peripheral wall to thereby define a portion of said air passage chamber with a free end of said conduit defining said outlet.

5. A device as in claim 4, in combination with the object, said object consisting of a circular petri dish having an upstanding peripheral wall and a microbial growth medium deposited therein.

6. A device as in claim 3, wherein said housing further includes a barrier wall mounted at least in proximity to said peripheral wall to define a portion of said air passage chamber.

7. A device as in claim 6, in combination with the object, said object consisting of a circular petri dish having an upstanding peripheral wall and a microbial growth medium deposited therein.

8. A device as in claim 6, wherein said drive mechanism consists of a motor mounted to said housing with a driven rotating shaft extending therefrom and through said barrier wall into said air passage chamber, and said hub is fixed to said shaft.

9. A device as in claim 8, in combination with the object, said object consisting of a circular petri dish having an upstanding peripheral wall and a microbial growth medium deposited therein.

10. A device as in claim 8, further including control means operatively connected to said motor for controlling operation of said motor.

* * * * *